(12) United States Patent
Hayes

(10) Patent No.: US 6,602,256 B1
(45) Date of Patent: *Aug. 5, 2003

(54) BONE STABILIZATION PLATE WITH A SECURED-LOCKING MECHANISM FOR CERVICAL FIXATION

(75) Inventor: Kyle Hayes, Mission Viejo, CA (US)

(73) Assignee: Cross Medical Products, Inc., Irvine, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 09/685,708

(22) Filed: Oct. 10, 2000

Related U.S. Application Data

(63) Continuation-in-part of application No. 09/415,805, filed on Oct. 11, 1999, now Pat. No. 6,224,602.

(51) Int. Cl.⁷ .............................................. A61B 17/80
(52) U.S. Cl. ....................................................... 606/69
(58) Field of Search ............................ 606/60, 69, 70, 606/71, 61; 623/11.11, 16.11

(56) References Cited

U.S. PATENT DOCUMENTS

| | | | |
|---|---|---|---|
| 2,443,363 A | * 6/1948 | Townsend et al. ............ | 606/69 |
| 5,951,558 A | 9/1999 | Fiz | |
| 6,136,002 A | * 10/2000 | Shih et al. ..................... | 606/61 |
| 6,224,602 B1 | * 5/2001 | Hayes ........................... | 606/69 |
| 6,235,034 B1 | * 5/2001 | Bray ............................. | 606/71 |

| | | | |
|---|---|---|---|
| 2002/0120273 A1 | * 8/2002 | Needham et al. ............. | 606/61 |

FOREIGN PATENT DOCUMENTS

FR     2 778 088 A1     4/1998

OTHER PUBLICATIONS

International Search Report.

* cited by examiner

Primary Examiner—Eduardo C. Robert
(74) Attorney, Agent, or Firm—Hudak, Shunk & Farine Co.; Laura F. Shunk

(57) ABSTRACT

A bone plate assembly is provided having a fixation plate held in position in a bone by a plurality of fasteners. The fasteners extend through holes in the bone plate to engage the bone below. Further, the assembly includes a locking plate, which is secured to the fixation plate by a lock screw or in a further embodiment by a mechanically biased detent extending into a hole in the locking plate. The lock plate can also include a divot, which is shallower than the hole to hold the lock plate in a open position. Further, the locking plate has a dovetailed connection to engage the flanges defining the exterior edges of a channel and the fixation plate. The locking plate, thus, has a sliding connection from a first position where it has at least partial openings corresponding to the openings of the fixation plate for the fasteners, and optionally also for a graft screw. In a second position, the edge of the plate surrounding the opening overlaps the fastener openings so as to lock these openings against the fastener backing out. The locking plate lock screw opening is counter sunk in the second position to enable the lock screws with the exterior surface of the locking plate.

10 Claims, 4 Drawing Sheets

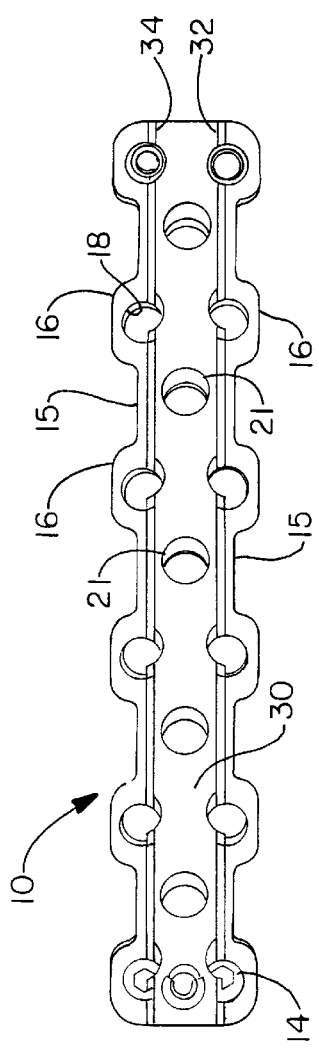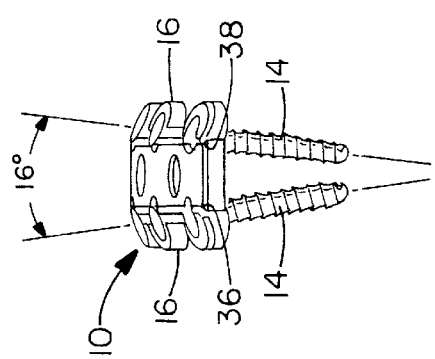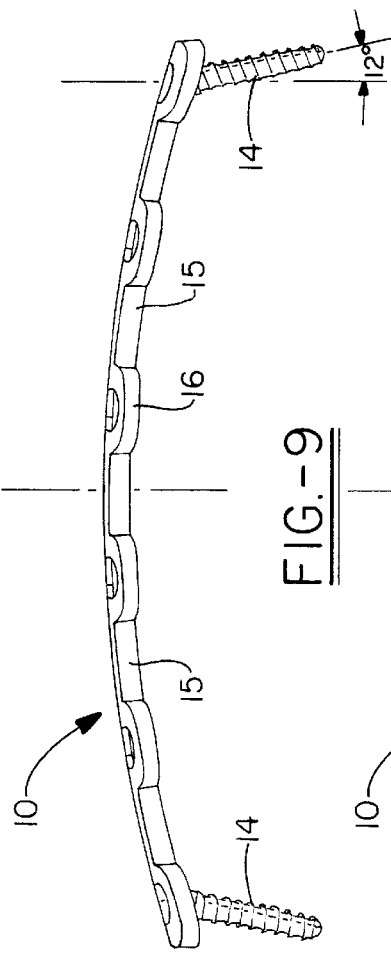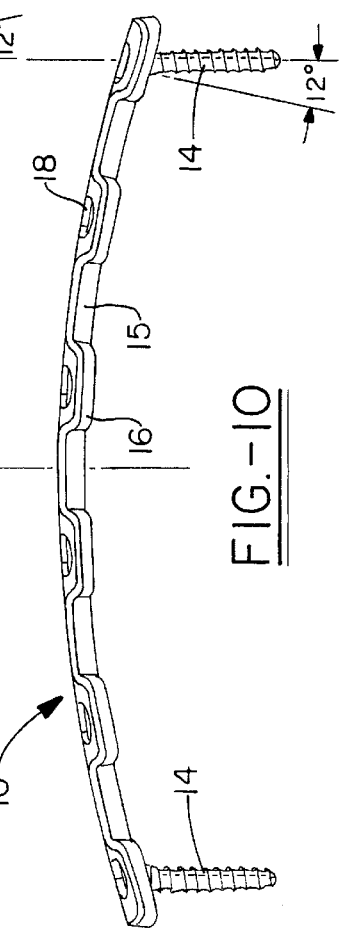

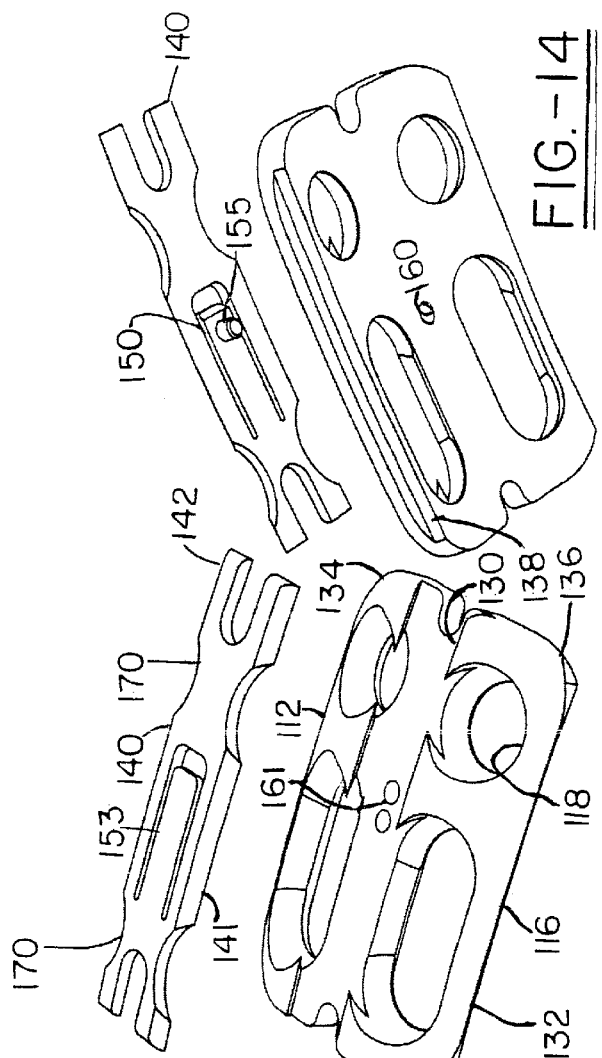
FIG.-14
FIG.-13
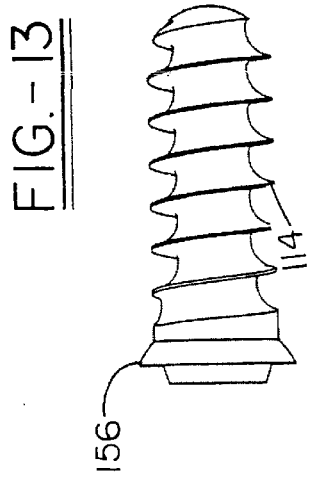
FIG.-15
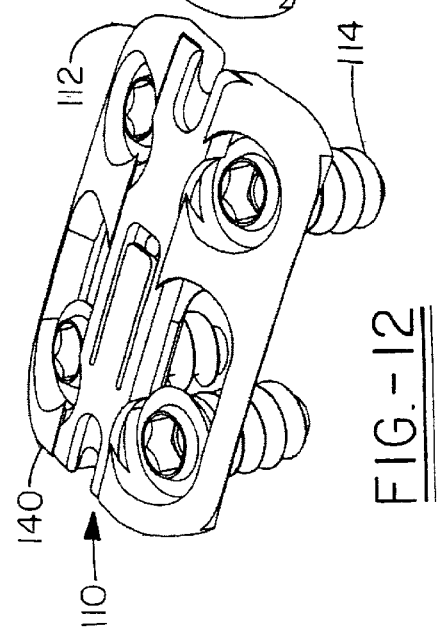
FIG.-12

BONE STABILIZATION PLATE WITH A SECURED-LOCKING MECHANISM FOR CERVICAL FIXATION

This application is a Continuation-in-Part application of U.S. patent application Ser. No. 09/415,805 filed Oct. 11, 1999, now U.S. Pat. No. 6,224,602, for a "Bone Stabilization Plate with a Secured Locking Mechanism."

FIELD OF THE INVENTION

The invention relates generally to a temporary orthopaedic plate device used for fixation and stabilization of one or more bone fragments with a means to secure and lock the fixation fastener to the plate to prevent the fixation fastener from backing out of the bone. In particular, the device is a fixation plate that contains a dovetail groove along the longitudinal axis that can accept a sliding lock plate with a dovetail shaped cross section. Initially the lock plate is secured (or tethered) to the fixation plate so that it has a limited amount of relative movement but together the two plates form a unit.

The dovetail shaped sliding lock plate contains a slot, referred to herein as a lock slot. This slot includes a conical shaped countersink located coaxially at one end of the slot. The lock slot allows a conical headed screw to pass through it and to be inserted into a threaded recess of the fixation plate to secure the sliding lock plate and limit its movement from one end of the lock slot to the other end of the lock slot. The sliding lock plate also contains cutouts and through holes to allow fixation fasteners to be placed through and into the holes in the fixation plate and in turn into the bone or graft material.

Sliding the lock plate to one end of the lock slot allows the cutouts and through holes to align with the fixation holes in the fixation plate. Sliding the lock plate to the other end of the lock slot allows the edges of the sliding lock plate to overlap over the holes in the fixation plate to secure the fixation screws and prevent the heads of fixation screws from backing out of the plate construct. It is when the sliding lock plate is slid to this position that the conical shaped countersink in the sliding lock and the conical headed lock screw align to cam the lock plate into position so as to lock down or fix the sliding lock plate into position in the fixation plate. Thus, the lock plate no longer slides relative to the fixation plate.

In a further embodiment of the invention, instead of using a lock screw to secure the lock plate into position, a spring biasing member is formed in the plate by forming a cut-out. The spring biasing member includes a boss which is held in a divot in the stabilization plate when the lock plate is in a first or "open" position so that the screws can be implanted. This divot is shallow enough to allow the plate to be easily pushed into the "closed" position where the boss encounters a deeper lock hole, which locks the plate, and thereby also the screws into position. The head of the bone anchor screws have a special step cut around the top to allow room for the lock plate without requiring the screws to be driven to an exact depth.

BACKGROUND OF THE INVENTION

Orthopaedic implants have evolved into many types of devices to assist in arthrodesis and correction of bone defects of a congenital, degenerative, or trauma related nature. Among the various types of orthopaedic implants are plate type devices. Plate type devices, like most devices, with the exception of endoprotheses, are temporary devices attached to stabilize two bone fragments or two bones, such as vertebra, until healing of the fragments or fusion of the two bones has occurred.

These devices are designed to be load sharing rather than load bearing. Load bearing devices typically carry all or bear all the stress. This is sometimes referred to as "stress shielding". Load sharing transfers some amount of the stress from the device to the bone itself. This transfer of load to the bone causes stress and this stress becomes the mechanism that triggers the body to start the healing or fusion process.

Some applications require different types of fastener devices, such as screws, pins, staples, or cerclage wire, in conjunction with the plate devices to secure them to the bone to provide the required stabilization. Many fasteners are designed specifically for the two different types of bone within the body.

The two types of bone are cortical and cancellous bone. Cortical bone is typically the hard, dense shell of the bone that provides the structural strength. Cancellous bone is the more spongy and soft bone located inside the cortical shell as part of the marrow of the bone, which provides the blood supply and nutrients for the bone.

Due to the hard, dense shell cortical bone is typically more stable for the placement of screws for fixation. Cancellous bone is weaker compared to cortical bone. Screws designed for fixation in cortical bone are typically placed through one cortex, through the cancellous or marrow, and into the far cortex of the bone. This is referred to as bicortical screw fixation. Screws designed for cancellous bone are typically designed with a buttress type thread to be able to put as much material as possible between successive threads to increase the shear area in the cancellous bone. Cancellous screws are typically placed through one cortical wall and sized in length such that the end or tip of the screw does not encounter the cortex on the far side of the bone but ends in the cancellous structure. Cancellous screws may be used instead of cortical screws when penetrating the far cortex is not preferable. In some cases, penetrating the far cortex may result in damage to arterial or neurological structures. However, one concern of screws placed unicortically into cancellous bone can be the tendency for the screw to "back out" from the plate device under cyclic loading and/or osteoporotic conditions or due to poor quality of the bone.

Devices used in applications involving the fusion or arthrodesis of two bones, such as the vertebra, require the cartilaginous material to be removed between them and the bone surface abraided to encourage a bleeding surface. Blood supply from the bleeding surfaces are required in order for the bone to fuse. Fusion of a joint involves removing the cartilaginous material in the joint and requires the cartilaginous surface of the articular joint to be abraided to encourage a bleeding surface for fusion. Fixation and stabilization must be adequate for the time required for a fracture to heal or two bones to fuse.

In certain applications where the devices are used in close proximity to a joint, the device should be designed such that it does not cause damage or have adverse effects to the articular surfaces of the joint. Further considerations of implant design should also be given to ensure that ligaments and tendon structures, usually located close to the joint, that come into contact with the implant are not compromised in any way by excess material, rough surfaces, or sharp edges. The profile of the present plate construct has been designed with these considerations.

SUMMARY OF THE INVENTION

In one embodiment, an anterior cervical plate assembly is provided with a fixation plate having exterior flanges each having a spherical counter sunk through hole to receive a cancellous screw for fixation. Recessed cutouts between these flanges provide for an increased ability to view the implantation site during fixation. These cutouts also allow easier bending by reducing the cross section of the plate. Further, the plate may include an additional aperture for fixation of a graft screw in the event a graft is used with the invention. Additionally, the top surface of the plate includes a channel defined by opposing undercut flanges, which form a sliding dovetail connection with mating edges of a locking plate. The locking plate further includes openings located to correspond and give access to the cancellous screw openings of the fixation plate when the locking plate is in a first position. This position is defined by a lock slot which receives a swaged lock screw, secured in the fixation plate. The locking plate can be slid to a second position where it does not overhang the fixation plate, and which is defined by the other end of the lock slot. In this position, the lock screw encounters a counter sink so that it can be tightened into a flush position relative to the top of the locking plate. The screw head includes a corresponding bevel to bias the locking plate into the second position in the countersink of the locking plate. Further in the second position of the locking plate, the bottom surfaces surrounding the edges of the cancellous-screw apertures now press against the top surfaces of the fixation plate surrounding the cancellous screws apertures. This blocks the heads of the cancellous screw from backing out of their apertures and locks them into position in the plate. The graft screw is, likewise, locked into place by the single sliding motion of the locking plate.

In a further embodiment of the invention, the locking plate has a leif spring formed in it by cutting a u-shape in the central portion of the plate. The spring has a boss on its bottom side which interfaces with a lock hole in the plate to lock it into the closed position, and with a shallower divot to hold the lock plate in an open position. The screws also have a step cut to allow more clearance for the plate.

BRIEF DESCRIPTION OF THE DRAWINGS

FIG. 8 is a top plan view of a second embodiment of the invention;

FIG. 9 is a side plan view of the embodiment of FIG. 8 with the superior and inferior screws in a first position;

FIG. 10 is a side plan view of the embodiment of FIG. 8 with the superior and inferior screws in a second position;

FIG. 11 is an end view of the embodiment of FIG. 8 plate into the second position;

FIG. 12 is a top perspective of a further embodiment of the invention with the lock plate in a closed position;

FIG. 13 is a top exploded view showing the stabilization plate and the lock plate;

FIG. 14 is bottom exploded view showing the assembly of the present invention; and FIG. 15 is a side view of the anchor screw in accordance with a further embodiment of the present invention.

DETAILED DESCRIPTION OF THE INVENTION

Figure 1:
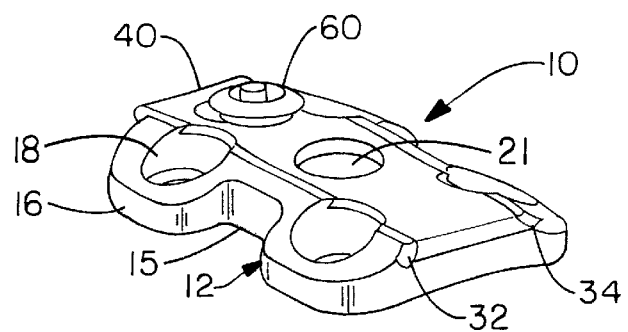
FIG. 1 is perspective view of a first embodiment of the invention.
Figure 2:
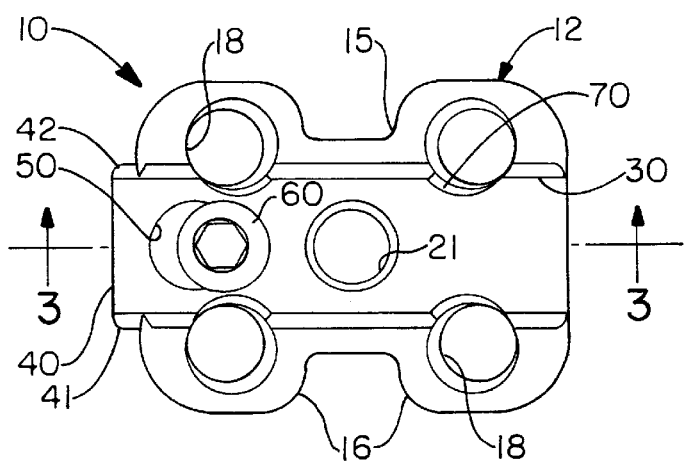
FIG. 2 is a top plan view of the invention of FIG. 1, with the locking plate in a first position.
Figure 3:
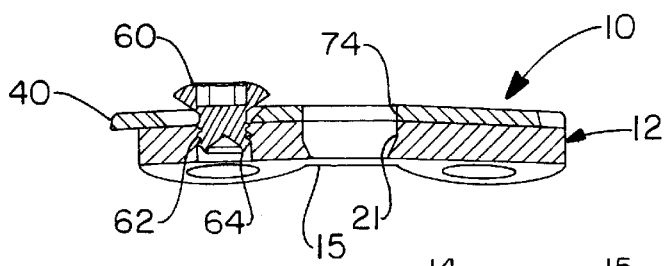
FIG. 3 is a cross-section of the invention of FIG. 2 taken along line 3—3.
Figure 4:
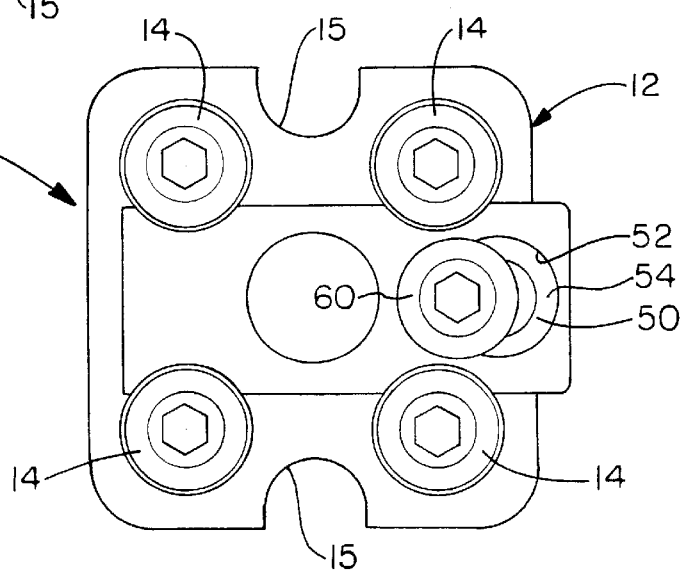
FIG. 4 is a top plan view of the invention with the locking plate in a first position.

As can be seen in FIG. 1, a bone fixation assembly is shown generally at 10 and includes a fixation plate 12 to be secured in an appropriate orthopedic setting by fastener means which are specifically cancellous screws 14, but could include other mechanical fixation means. Specifically, a fixation plate 12 includes exterior flanges 16 having spherical countersunk through bores 18 which receive the cancellous screws 14. The plate 12 also includes an aperture 21 for a graft screw.

Between each of respective flange pairs, the plate includes an undercut 15 to give the surgeon better viewing access to the implantation site. The top surface of the flanges are slightly tapered and rounded in order to minimize hard edges and as well as unnecessary material. Further, as can be seen, the fixation plate includes a slight arch along its longitudinal length in order to best accommodate a vertebral application in particular, for anterior application in the cervical spine. Thus, the curve is a sagittal curve. The plate can be presented in various lengths expanding from 2–5 vertebrae.

On its upper surface, the fixation plate includes a channel 30, which is defined by opposing flanges 32, 34 each having an undercut 36–38, which will provide for a dovetailing connection with a corresponding edge 41, 42 of a locking plate 40. It can be envisioned thus, that the locking plate has a width and thickness to provide for a relatively easy sliding motion within the channel of the fixation plate. This cooperation between the locking plate and the fixation plate substantially restricts the locking plate to a single degree of freedom, along the longitudinal axis of the two plates.

Further, the locking plate includes a slot or opening 50 having a first end 51, which provides a positive stop to define the first unlocked position, and a second end 52 to define a second locked position. The second end 52 of the slot 50 includes a counter sink 54, which allows the lock screw 60 to be tightened into a flush position relative to the exterior surface of the locking plate. Lock screw 60 extends through the slot 50 into a threaded recess 62 in the fixation plate. Recess 62 includes a through bore to allow the bottom surface of the setscrew 60 to be swaged upward to form a rim 64, which locks the setscrew in position so that it cannot escape the aperture 62 when it reaches the full extent of its vertical play. Thus, the lock screw 60 acts with the lock slot for the locking plate to define the extent of both vertical and longitudinal movement relative to the fixation plate. This interaction also unites the assembly to provide a unit of interacting components, which are easily manipulated during the implantation surgery.

Figure 5:
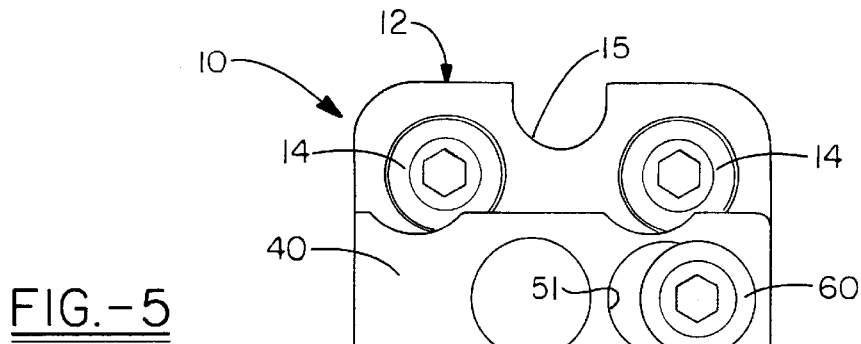
FIG. 5 is a top plan view of the invention with the locking plate in a second position.
Figure 6:
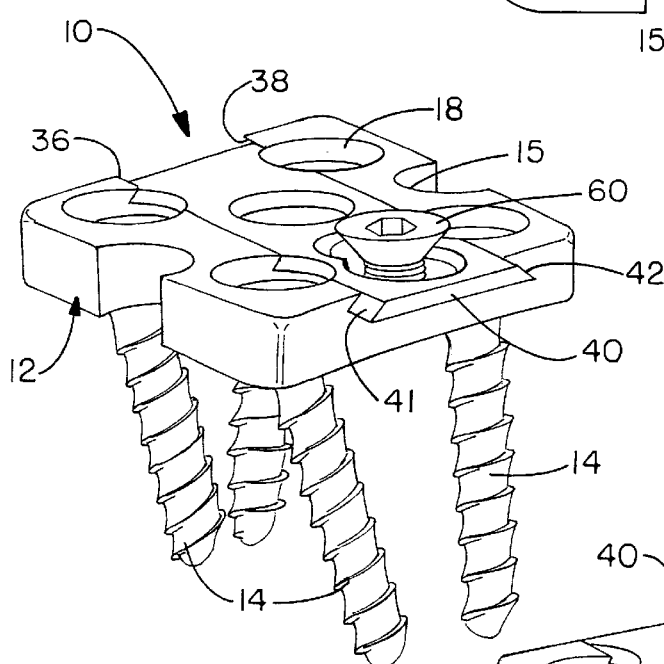
FIG. 6 is a side perspective view with the locking plate in the first position.
Figure 7:
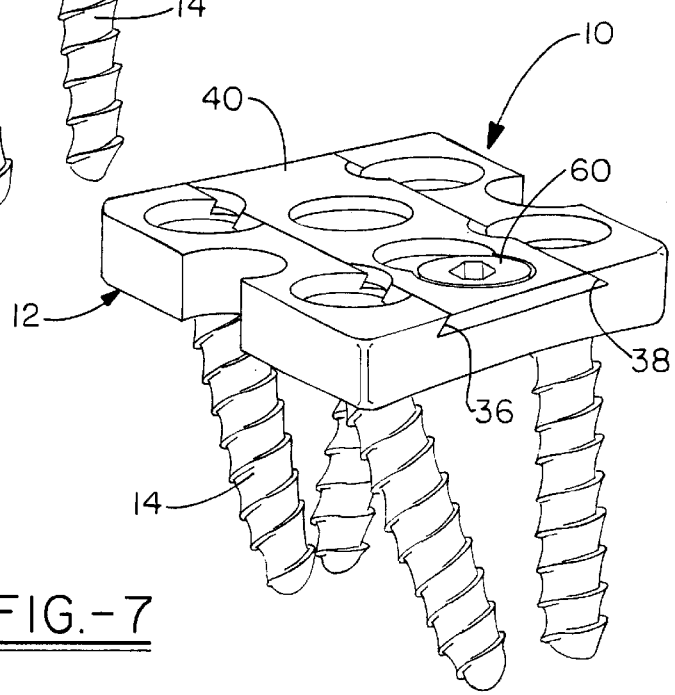
FIG. 7 is a side perspective view with the locking plate in the second position.

Locking plate 40 further includes a series of semi-circular open areas 70, which correspond when the locking plate is in its first position to the openings 18 for the cancellous screws in the fixation plate. In the second position, as can be best seen in FIG. 5, the bottom surface of the locking plate 40 in the vicinity of the opening 18 overlap the cancellous screw holes so as to restrain the screws from backing out of the fixation plate. A similar opening 74 is provided for the graft screw, which is available in the internal portion of the plate. Thus, it can be seen, that when the locking plate is slid from its first position to its second position, a plurality, and in fact all, of the screws of the fixation plate can be locked into position.

FIGS. 12–14 illustrate a further embodiment of the invention and more specifically show a bone fixation assembly is shown generally at 110. The assembly includes a fixation plate 112 to be secured by fastener means which are specifically cancellous screws 114, but could include other mechanical fixation means. Once again, the fixation plate 112 includes exterior flanges 116 having countersunk through bores 118 which receive the screws 114.

The fixation plate includes a central longitudinal channel 130, which is defined by opposing flanges 132, 134 each having an undercut 136, 138, which will provide for a dovetailing connection with a corresponding edge 141, 142 of a locking plate 140. Thus, the locking plate is captured by and slides in the central channel 130.

Locking plate 140 further includes a series of semi-circular open areas 170, which correspond when the locking plate is in its first position to the openings 118 for the screws. In the second position, as can be best seen in FIG. 12, the bottom surface of the locking plate 140 in the vicinity of the openings 118 overlap the screw holes so as to restrain the screws from backing out of the fixation plate.

The locking plate also includes a snap lock locking mechanism, which includes a lief spring 153 formed by u-shaped slits 150 in the lock plate. An enlarged recess 151 in the bottom of the U allows room to lift the lief spring 153 upward to disengage the locking mechanism. The lief spring includes a boss 155 on its bottom surface, which snaps into a through hole 160 in the lock plate to lock the plate into the closed position. There is also a divot 161, which is shallower than the hole 160, which captures the boss. This holds the plate in an open position of the lock plate where the screw holes are accessible to the surgeon. However, the boss can be disengaged by sliding it forward past the divot into the hole.

Also the further embodiment includes a step cut profile for the screw, which has a lower profile. The head has an exterior flange 156, which surrounds the head which projects upward beyond the flange to form the portion of the screw, which is captured by the lock plate. The corner of the lock plate engages the upper edge surface of the screw head.

Once the surgical exposure is complete and the final size implant is chosen, the implants are secured and fixated by use of the required instrumentation. Initially, appropriately placed and sized holes are tapped for screw placement.

Once tapping is complete, the appropriate length screw is chosen and attached to the hex of the screwdriver bit and the screwholder is applied to hold the screw until placed.

The screw is then placed through the holes in the plate and then advanced until the head of the screw is securely seated in the spherical countersink of the plate. This procedure is repeated for the number of screws being placed or required for secure fixation.

The graft screw is then placed through one of the holes along the centerline (sagittal plane) and then advanced until the head of the screw is securely seated in the spherical countersink of the plate in order to secure graft material, whether autogenous, allograft, or substitute.

The vertebral screws and the graft screws are secured in the bone and plate by advancing the lock plate until the conical head of the lock screw lines up with the conical countersink in the lock slot of the lock plate. The lock screw is then advanced until seated. The screws will not back out of the plate once the slider plate is in position due to the plate overlapping one edge of each hole.

Once all plates and screws are secure according to the preoperative plan, wound closure can proceed by or under the direction of the surgeon.

While in accordance with the patent statutes the best mode and preferred embodiment have been set forth, the scope of the invention is not limited thereto, but rather by the scope of the attached claims.

What is claimed is:

1. A bone plate comprising;
    a fixation plate defining at least one through bore through which at least one screw is inserted to fix the plate to a bone, and a lock plate having a sliding engagement with the fixation plate and being longitudinally adjustable from a first position in which the through bore is accessible to the screw to a second position in which the lock plate retains the screw from backing out of the bone, one of said lock plate and said fixation plate having a channel which receives the other of said lock plate and said fixation plate to form said sliding engagement, and said channel including a dovetail which receives a flange.

2. A bone plate as set forth in claim 1, wherein the vertical freedom is defined by a lock screw which extends through an opening in the lock plate to secure the lock plate to the fixation plate.

3. A bone plate as set forth in claim 2, wherein the lock plate includes a slit to define a lief spring which includes said boss.

4. A bone plate as set forth in claim 3, wherein the boss is on the underside of the lock plate.

5. A bone plate as set forth in claim 4, wherein the recess is formed on the top side of the fixation plate.

6. A bone plate as set forth in claim 5, wherein said fixation plate further includes a first recess which receives the boss to hold the lock plate in the first position and a second recess which receives the boss to hold the lock plate in the second position.

7. A bone plate as set forth in claim 6, wherein said screw has a step cut head.

8. A bone plate as set forth in claim 2, wherein the sliding connection is formed by providing opposing shoulders in the top of the fixation plate so as to define a guide way for the lock plate.

9. A bone plate as set forth in claim 8, wherein the guide way includes opposing undercuts to restrain the locking plate vertically as well as laterally.

10. A bone plate as set forth in claim 1, wherein said bone plate includes multiple screws and said lock plate can simultaneously lock multiple screws into position.

\* \* \* \* \*

UNITED STATES PATENT AND TRADEMARK OFFICE
CERTIFICATE OF CORRECTION

PATENT NO. : 6,602,256 B1  Page 1 of 1
APPLICATION NO. : 09/685708
DATED : August 5, 2003
INVENTOR(S) : Kyle Hayes It is certified that error appears in the above-identified patent and that said Letters Patent is hereby corrected as shown below:

Column 3
Line 32, delete "leif" and insert --leaf--.

Column 5
Line 23, delete "lief" and insert --leaf--.

Column 5
Line 25, delete "lief" and insert --leaf--.

Column 5
Line 26, delete "lief" and insert --leaf--.

Column 6
Lines 29-32, Claim 2, delete "the vertical freedom is defined by a lock screw which extends through an opening in the lock plate to secure the lock plate to the fixation plate" and insert --the lock plate includes a boss, which cooperates with a recess in the fixation plate to secure the lock plate to the fixation plate--.

Column 6
Line 34, Claim 3, delete "leif" and insert --leaf--.

Signed and Sealed this

Nineteenth Day of May, 2009

JOHN DOLL
*Acting Director of the United States Patent and Trademark Office*